United States Patent [19]
Tani et al.

[11] Patent Number: 4,744,899
[45] Date of Patent: May 17, 1988

[54] STERILIZATION OF ADSORBENT AND COLUMN HAVING IMPROVED STORABILITY INCLUDING STERILIZED ADSORBENT FOR USE IN EXTRACORPOREAL CIRCULATION TREATMENT

[75] Inventors: Nobutaka Tani, Minoo; Tsutomu Okuyama; Shigeo Furuyoshi, both of Kobe, all of Japan

[73] Assignee: Kanegafuchi Kagaku Kogyo Kabushiki Kaisha, Osaka, Japan

[21] Appl. No.: 789,540

[22] Filed: Oct. 21, 1985

[30] Foreign Application Priority Data

Oct. 22, 1984 [JP] Japan .................................. 59-221861
Oct. 22, 1984 [JP] Japan .................................. 59-221862

[51] Int. Cl.$^4$ .............................................. B01D 15/00
[52] U.S. Cl. .................................................. 210/263
[58] Field of Search ................................. 210/263, 927

[56] References Cited

U.S. PATENT DOCUMENTS 4,103,685 8/1978 Lupien et al. ..................... 210/927
4,252,653 2/1981 Beck et al. ......................... 210/927

Primary Examiner—Ivars Cintins
Attorney, Agent, or Firm—Armstrong, Nikaido, Marmelstein & Kubovcik

[57] ABSTRACT

A process for steam-sterilizing an adsorbent for use in extracorporeal circulation treatment comprising a water-insoluble support and a sulfated polysaccharide immobilized on the support, characterized by sterilizing the adsorbent in an aqueous medium maintainted at pH 5 to 9, whereby the sulfated polysaccharide is prevented from releasing from the support and being deactivated. When the water-insoluble support/sulfated polysaccharide adsorbent is packed in a column with an aqueous buffer solution having a pH 5 to 9 to provide an adsorption column for use in extracorporeal circulation treatment, release and deactivation of the sulfated polysaccharide are prevented and the column can be stored for a long term.

3 Claims, No Drawings

STERILIZATION OF ADSORBENT AND COLUMN HAVING IMPROVED STORABILITY INCLUDING STERILIZED ADSORBENT FOR USE IN EXTRACORPOREAL CIRCULATION TREATMENT

BACKGROUND OF THE INVENTION

The present invention relates to a process for sterilizing an adsorbent, and more particularly to a process for sterilizing an adsorbent for use in extracorporeal circulation treatment comprising a water-insoluble support and a sulfated polysaccharide attached to the support. The invention also relates to an adsorption column for use in extracorporeal circulation treatment having an improved storage stability.

Hitherto, for the purpose of selectively removing harmful substances from body fluid such as blood, it has been attempted to use an adsorbent comprising a water-insoluble support and, attached thereto, a material having a peculiar affinity for harmful substances, namely the so-called ligand, in extracorporeal circulation treatment. Sterilization of the adsorbent is indispensable for using it in the treatment. From the viewpoints of safety and handling upon use, sterilization by chemical reagents is inadequate and high pressure steam sterilization is preferred. However, the high pressure steam sterilization of adsorbents has the drawback that the ligand is deactivated or released from the support. In particular, it is known that for an adsorbent having a sulfated polysaccharide as a ligand is easy to cause decomposition such as desulfation by high pressure steam sterilization. If the water-insoluble support/sulfated polysaccharide adsorbent is sterilized under severe conditions, for example, at 121° C. for 20 minutes, the fixed sulfated polysaccharide is hydrolyzed to release from the support, thus the ability of removing harmful substances from body fluid is deteriorated.

An adsorbent is packed in a column with a packing fluid and is used for extracorporeal circulation treatment. Water is usually used as a packing fluid by the reasons that the use of water makes it unnecessary to dry the adsorbent which is usually steam-sterilized and is obtained in a wet state and that a packing fluid in an adsorption column is always once replaced with water before using in extracorporeal circulation treatment.

There is a case where the thus prepared adsorption column for extracorporeal circulation treatment is used after storing for a period as long as about 1 year. Therefore, it is required that the adsorbent performance is maintained for at least about 1 year.

The water-insoluble support/sulfated polysaccharide adsorbent has also another defect that when a column for extracorporeal circulation treatment use packed with the adsorbent and water is stored for a long term, the sulfated polysaccharide is hydrolyzed to release from the support and, moreover, the progress of the hydrolysis produces sulfuric acid compounds and they further accelerate the hydrolysis, thus resulting in deterioration of column performance.

It is an object of the present invention to provide a process for steam-sterilizing an adsorbent for use in extracorporeal circulation treatment comprising a water-insoluble support and a sulfated polysaccharide attached to the support without deteriorating the ability of removing harmful substances from body fluid such as blood.

Another object of the present invention is to provide a column for extracorporeal circulation treatment use having an improved storage stability, which is packed with a water-insoluble support/sulfated polysaccharide adsorbent and a packing fluid.

These and other objects of the present invention will become apparent from the description hereinafter.

SUMMARY OF THE INVENTION

It has now been found that a sulfated polysaccharide supported on a water-insoluble support is stable in an aqueous medium maintained at pH 5 to 9, and can stably be sterilized or stored under such a condition.

In accordance with one of the fundamental aspects of the present invention, there is provided an improvement in a process for steam-sterilizing an adsorbent for use in extracorporeal circulation treatment comprising a water-insoluble support and a sulfated polysaccharide immobilized on said support, the improvement which comprises sterilizing said adsorbent in an aqueous medium maintained at pH 5 to 9.

In another aspect of the invention, there is provided an adsorption column for use in extracorporeal circulation treatment comprising a column, an adsorbent packed in said column comprising a water-insoluble support and a sulfated polysaccharide immobilized on said support, and an aqueous internal packing fluid of pH 5 to 9 containing 0.001 to 10% by weight of a compound having a buffer action.

DETAILED DESCRIPTION

Examples of the sulfated polysaccharide used in the present are, for instance, heparin, dextran sulfate, chondroitin sulfate, chondroitin polysulfate, heparanic acid, keratin sulfate, heparitin sulfate, xylan sulfate, caronin sulfate, cellulose sulfate, chitin sulfate, chitosan sulfate, pectin sulfate, inulin sulfate, alginic sulfate, glycogen sulfate, polylactose sulfate, carrageenan sulfate, starch sulfate, polyglucose sulfate, laminarin sulfate, galactan sulfate, levan sulfate, mepesulfate, and the like. The sulfated polysaccharides used in the present invention are not limited to exemplified ones, any sulfated polysaccharides which have been generally used for the preparation of adsorbents for use in extracorporeal circulation treatment, can be used in the invention. Among the above-mentioned sulfated polysaccharides, heparin, dextran sulfate and chondroitin polysulfate are preferred.

As the water-insoluble support used in the present invention, there are mentioned, for instance, supports used generally in affinity chromatography, e.g. soft gels such as agarose, dextran and polyacrylamide, inorganic porous materials such as porous glass, porous silica and porous alumina, polymer gels made of synthetic polymers such as styrene-divinyl benzene copolymer, crosslinked polyvinyl alcohol and crosslinked polyacrylate, and porous cellulose gels such as cellulose, esterified cellulose and etherified cellulose. Of course, it is to be understood that the water-insoluble supports used in the invention are not limited to those set forth above. Among them, hard gels such as the inorganic porous materials and the polymer hard gels are preferred, since a sufficient flow of body fluid is obtained and choking is hard to occur. In particular, the porous cellulose gels are preferred for the reasons that (1) they are hard to be broken into pieces or fine powder by operation such as agitation because of a relatively high mechanical strength and toughness, and also even if a body fluid is passed through a column packed therewith at a high flow rate, consolidation and choking do not occur and, therefore, it is possible to pass a body fluid at a high flow rate, and further the pore structure is hard to suffer change upon high pressure steam sterilization, (2) the gels are hydrophilic because of being made of cellulose and having plenty of hydroxyl group utilizable for bonding the sulfated polysaccharide, and also having a small nonspecific adsorption, (3) an adsorption capacity comparable to that of the soft gels is obtained, because the strength is maintained relatively high even if the porosity volume is increase, and (4) the safety is high as compared with the synthetic polymer gels. The porous cellulose gels on which the sulfated polysaccharides are immobilized provide adsorbents capable of selectively removing harmful substances at a high flow rate. Adsorbents prepared from porous cellulose gel supports are disclosed in detail in Japanese Unexamined Patent Publication (Tokkyo Kokai) No. 193135/1984. and they are of course used in the invention.

The adsorbent for extracorporeal circulation treatment use is prepared by immobilizing the sulfated polysaccharide as ligand to the water-insoluble support. The immobilization can be made by various known methods such as a physical fixing method, an ionic coupling method and a covalent coupling method. Since it is important that the immobilized ligand is hardly released from the support, covalent coupling which attains strong fixing is preferable. Even if other fixing means than covalent coupling are adopted, it is desirable to have means for preventing the ligand from releasing. Also, a spacer may be introduced between the support and the ligand, as occasion demands.

The adsorbent is steam-sterilized generally in an autoclave. In the present invention, the steam-sterilization is conducted in the state that the adsorbent is in an aqueous medium which is maintained at pH 5 to 9 during the sterilization, under usual temperature and time conditions, for instance, at about 121° C. for about 20 minutes. When the pH of the aqueous medium in steam sterilization is less than 5, the adsorption activity of the adsorbent is lowered markedly or the immobilized ligand is markedly hydrolyzed and released from the support. The same phenomena as above are observed also when the pH is more than 9. In the former case, lowering of the adsorption activity mainly occurs, and in the latter case, release of the ligand due to hydrolysis mainly occurs. In both cases, the performance of the adsorbent is lowered. Preferably, the change in pH between the original pH and the pH at the end of sterilization is at most 1.5.

A method for controlling the pH of the aqueous medium used in steam sterilization is not particularly restricted. For instance. the pH controlling may be conducted by automatically observing the change in pH during the sterilization, and adjusting to a pH as near the original pH as possible, for instance, by adding a basic or acidic compound to the aqueous medium with every slight pH change. Preferably, the pH controlling is conducted by using a compound having a buffer action (hereinafter referred to as "buffer"). Satisfactory results are obtained by steam-sterilizing the adsorbent in an aqueous buffer solution and also such a method has the advantages that the pH controlling is stably attained without requiring a special apparatus, and that the aqueous buffer solution used in sterilization can be used as a storage liquid for the sterilized adsorbent or as a packing fluid for an adsorption column, whereby lowering in activity and release of ligand caused by pH change during the storage are also prevented.

In an embodiment of the present invention. the steam-sterilization of the adsorbent is carried out by packing the adsorbent particles in an adequate container, e.g. a column. with an aqueous buffer solution within the range of pH 5 to 9, placing the container in an autoclave, and introducing high pressure steam to the autoclave to externally heat the container to a sterilizing temperature for a predetermined time sufficient to attain the sterilization. The aqueous buffer solution introduced into the container may be a heated hot solution.

Any compounds having a buffer action can be used in the invention for preparing an aqueous buffer solution used as the aqueous medium in the sterilization. Preferably, compounds safe for human body are used as buffers, for example, citric acid, phosphoric acid, acetic acid, boric acid, tartaric acid, carbonic acid, maleic acid, glycine, the sodium, potassium and calcium salts of these acids, and mixtures of these acids and salts.

The concentration of the buffer solution used in the sterilization is not particularly limited, so long as it serves as the buffer solution. Preferably, from the viewpoint of easiness in cleaning of the adsorbents conducted when using them for extracorporeal circulation treatment, the concentration of the buffer in the solution is selected from 0.001 to 10% by weight, especially from 0.01 to 2% by weight.

The sterilized adsorbent particles are packed in a column, for example, a column provided, at its inlet and outlet, with a filter or a mesh, and are used for purposes such as extracorporeal circulation treatment by putting the column in extracorporeal circulation circuit and passing body fluid such as blood or plasma through the column.

According to another aspect of the present invention, it is possible to improve the storage stability of the adsorbent by storing the adsorbent in an aqueous solution containing 0.001 to 10% by weight. preferably 0.01 to 2% by weight, of a buffer. Thus, the present invention also provides a column for use in extracorporeal circulation treatment having an improved storage stability.

The adsorption column for extracorporeal circulation treatment use of the present invention is prepared by packing steam-sterilized adsorbent particles in an adequate column with a 0.001 to 10% by weight aqueous buffer solution as an internal packing fluid. When the concentration of the buffer in the solution is less than 0.001% by weight, it is difficult to keep the desired pH for a long term. When the concentration is more than 10% by weight, a longer time is required in cleaning the packed adsorbent which must be done before using the column, and also a buffer may deposit during storage.

Although the adsorbent steam-sterilized in water or in other manners than the above-mentioned can of course be used in the preparation of the column, the adsorbent sterilized in the above-mentioned manner is preferred. The steam sterilization according to the invention is advantageous also from the point of preparing the column, since the aqueous buffer solution used in sterilization can be utilized as a packing fluid for the column, in addition to prevention of deactivation and release of the ligand.

The column is usually stored under mild conditions unlike the high pressure steam sterilization. Therefore, the object of the invention can be attained by using the aqueous buffer solution having a pH of 5 to 8.5. According to the present invention, the column can be stored for a long term without lowering the adsorption activity and releasing the ligand from the support.

The present invention is more specifically described and explained by means of the following Examples in which all % are by weight unless otherwise noted. It is to be understood that the present invention is not limited to the Examples.

In order to illustrate the preparation of adsorbents, Reference Examples are also given below.

REFERENCE EXAMPLE 1

To 10 ml of particles of a crosslinked polyacrylate gel (commercially available under the trademark "Toyopearl HW75" made by Toyo Soda Manufacturing Co., Ltd.) (hard gel having pores uniformly in the whole, protein exclusion limit: $5 \times 10^7$, particle size: 50 to 100 μm) were added 6 ml of a saturated aqueous NaOH solution and 15 ml of epichlorohydrin. The reaction was carried out at 50° C. for 2 hours with agitation to give epoxidized gel. To the resulting gel was added 20 ml of concentrated aqueous ammonia, and the mixture was agitated at 50° C. for 2 hours to introduce amino group into the gel.

In 10 ml of water was dissolved 200 mg of heparin, and after adjusting the resulting solution to pH 4.5, 3 ml of the above gel having amino group was added to the solution. To the mixture was added 200 mg of 1-ethyl-3-(dimethylaminopropyl)carbodiimide, while maintaining the mixture at pH 4.5, and the mixture was then shaken at 4° C. for 24 hours. After the completion of the reaction, the gel was washed with 2M aqueous NaCl solution, 0.5M aqueous NaCl solution and water in that order to give a heparin-immobilized gel (hereinafter referred to as "A-1").

REFERENCE EXAMPLE 2

To 10 ml of Toyopearl HW75 (crosslinked polyacrylate gel) were added 6 ml of a saturated aqueous NaOH solution and 15 ml of epichlorohydrin. The reaction was carried out at 50° C. for 2 hours with agitation, and the gel was washed successively with an alcohol and water to give an epoxidized gel.

To 2 ml of the resulting wet gel (solid content: about 30%) were added 0.5 g of sodium salt of dextran sulfate (intrinsic viscosity: 0.055 dl/g, average degree of polymerization: 40, sulfur content: 19%) and 2 ml of water (concentration of sodium salt of dextran sulfate: about 13%). The mixture was adjusted to pH 12, and subjected to reaction at 40° C. for 16 hours with shaking. The gel was filtered and washed with 2M aqueous NaCl solution, 0.5M aqueous NaCl solution and water in that order to give a sodium dextran sulfate-immobilized gel (hereinafter referred to as "A-2").

REFERENCE EXAMPLE 3

The procedure of Reference Example 2 was repeated except that heparin was used instead of sodium dextran sulfate to give a gel on which heparin was immobilized (hereinafter referred to as "A-3").

REFERENCE EXAMPLE 4

Porous glass beads (commercially available under the trademark "FPG 2000" made by Wako Pure Chemical Industries, Ltd., average pore size: 1.950 angstroms, specific surface area: 13 m²/g, particle size: 80 to 120 meshes) were heated in diluted nitric acid for 3 hours. After washing with water and drying, the beads were heated at 500° C. for 3 hours. The beads were then added to a 10% solution of γ-aminopropyltriethoxysilane in toluene, reacted for 3 hours under reflux, and washed with methanol to give a γ-aminopropyl-treated glass beads.

In 10 ml of water was dissolved 200 mg of heparin, and after adjusting the resulting solution to pH 4.5, 2 g of the treated glass beads was added to the solution. To the mixture was added 200 mg of 1-ethyl-3-(dimethylaminopropyl)carbodiimide, while maintaining the mixture at pH 4.5, and the mixture was shaken at 4° C. for 24 hours. After the completion of the reaction, the glass beads were washed with 2M aqueous NaCl solution, 0.5M aqueous NaCl solution and water in that order to give a heparin/porous glass adsorbent (hereinafter referred to as "B-1").

REFERENCE EXAMPLE 5

The procedure of Reference Example 4 was repeated except that chondroitin polysulfate was used instead of heparin, to give a chondroitin polysulfate-immobilized glass beads (hereinafter referred to as "B-2").

REFERENCE EXAMPLE 6

In 10 ml of a 0.25M aqueous solution of NaIO$_4$ was dissolved 800 mg of dextran sulfate, and the resulting solution was agitated at room temperature for 4 hours. To the reaction mixture was added 200 mg of ethylene glycol, and the mixture was further agitated for 1 hour. After adjusting the reaction mixture to pH 8, thereto was added 4 ml of γ-aminopropyl-treated glass beads prepared in the same manner as in Reference Example 4, and the mixture was shaken for 24 hours. After the completion of the reaction, the glass beads were filtered and washed with water, and then suspended in 10 ml of a 1% aqueous solution of NaBH$_4$ for 15 minutes for reduction reaction. The beads were filtered and washed with water to give a dextran sulfate/porous glass adsorbent (hereinafter referred to as "B-3").

REFERENCE EXAMPLE 7

Porous glass beads FPG2000 were heated in diluted nitric acid for 3 hours, washed with water and heated at 500° C. for 3 hours. The beads were added to a 10% toluene solution of γ-glycidoxypropyltrimethoxysilane, reacted under reflux for 3 hours and washed with methanol to give γ-glycidoxypropyl-treated glass beads.

In 10 ml of water was dissolved 2 g of dextran sulfate, and after adjusting the resulting solution to pH 9.2, thereto were added 2 g of the treated glass beads, and the reaction was conducted at 45° C. for 16 hours. After the completion of the reaction, the beads were washed successively with 2M aqueous NaCl solution, 0.5M aqueous NaCl solution and water to give dextran sulfate-immobilized glass beads (hereinafter referred to as "B-4").

REFERENCE EXAMPLE 8

To 10 ml of a porous cellulose gel (commercially available under the trademark "CK Gel A-3" made by Chisso Corporation, exclusion limit molecular weight: $5 \times 10^7$, particle size: 45 to 105 μm) were added 4 g of a 20% aqueous NaOH solution, 12 g of heptane and a drop of a non-ionic surfactant (commercially available under the trademark "Tween 20" made by Kao Atlas Kabushiki Kaisha). The mixture was agitated at 40° C. for 2 hours, and after adding 5 g of epichlorohydrin, it was further agitated for 2 hours. The gel was washed with water and filtered to give an epoxidized cellulose gel. The amount of epoxy group introduced was 30 μM per 1 ml of bed volume.

To 2 ml of the obtained wet gel were added 0.12 g of sodium salt of dextran sulfate (intrinsic viscosity: 0.027 dl/g, sulfur content: 17.7%) and 2 ml of water (concentration of sodium dextran sulfate: about 2.5%). The mixture was adjusted to pH 11 and shaken at 45° C. for 16 hours. The gel was filtered and washed with 2M aqueous NaCl solution, 0.5M aqueous NaCl solution and water in that order to give a sodium dextran sulfate/cellulose gel adsorbent (hereinafter referred to as "C-1").

REFERENCE EXAMPLE 9

CK Gel A-3 (cellulose gel) was filtered with suction, and to 10 g of the filtered gel were added 4 g of a 20% aqueous NaOH solution, 12 g of heptane and a drop of non-ionic surfactant Tween 20, and the mixture was then agitated to disperse the gel. The mixture was agitated at 40° C. for 2 hours, and 5 g of epichlorohydrin was added to the mixture and agitation was further continued at 40° C. for 2 hours. The reaction mixture was allowed to stand and the resulting supernatant was discarded. The obtained gel was washed with water and filtered to give an epoxidized gel. To the epoxidized gel was added 15 ml of concentrated aqueous ammonia, the mixture was agitated at 40° C. for 1.5 hours, filtered with suction and washed with water to give an amino group-introduced cellulose gel.

In 10 ml of water was dissolved 200 mg of heparin, and to the resulting solution was added the cellulose gel having amino groups. The mixture was adjusted to pH 4.5. and thereto was added 200 mg of 1-ethyl-3-(dimethylaminopropyl)carbodiimide while maintaining at pH 4.5. The mixture was then shaken at 4° C. for 24 hours. After the completion of the reaction, the reaction mixture was washed with 2M aqueous NaCl solution, 0.5M aqueous NaCl solution and water in that order to give a heparin-immobilized gel (hereinafter referred to as "C-2").

REFERENCE EXAMPLE 10

The procedure of Reference Example 8 was repeated except that chondroitin polysulfate was used instead of sodium dextran sulfate, to give a chondroitin polysulfate-immobilized cellulose gel (hereinafter referred to as "C-3").

REFERENCE EXAMPLE 11

The procedure of Reference Example 8 was repeated except that heparin was used instead of sodium dextran sulfate, to give a heparin-immobilized cellulose gel (hereinafter referred to as "C-4").

EXAMPLES 1 TO 18 AND COMPARATIVE EXAMPLES 1 TO 11

In a hard glass flask was placed 10 g (wet weight) of the adsorbent prepared in Reference Examples 1 to 11, and 10 ml of an aqueous medium shown in Table 1 was added to the flask. The flask was placed in an autoclave and was subjected to high pressure steam sterilization at 121° C. for 40 minutes.

The pH of the aqueous medium and the amount of the ligand immobilized to the support were measured before and after the sterilization. The amount of the ligand was calculated from the amount of Toluidine Blue adsorbed.

The results are shown in Table 1.

TABLE 1

| | Adsorbent | Aqueous medium | pH before | pH after | Amount of ligand (mg/ml) before | Amount of ligand (mg/ml) after | Retention rate of ligand (%) |
|---|---|---|---|---|---|---|---|
| Com. Ex. 1 | A-1 | water | 7.2 | 5.2 | 1.0 | 0.65 | 65 |
| Ex. 1 | A-1 | 1/15 M phosphoric acid buffer soln. | 7.4 | 7.2 | 1.0 | 0.90 | 90 |
| Com. Ex. 2 | A-2 | water | 7.2 | 3.2 | 0.9 | 0.15 | 16.6 |
| Ex. 2 | A-2 | 1/15 M phosphoric acid buffer soln. | 7.4 | 7.0 | 0.9 | 0.85 | 94.4 |
| Com. Ex. 3 | A-3 | water | 7.0 | 5.0 | 1.6 | 1.20 | 75 |
| Ex. 3 | A-3 | 1/15 M phosphoric acid buffer soln. | 7.4 | 7.1 | 1.6 | 1.55 | 96.8 |
| Com. Ex. 4 | B-1 | water | 7.5 | 5.0 | 1.3 | 0.85 | 65.3 |
| Ex. 4 | B-1 | 1/15 M phosphoric acid buffer soln. | 7.4 | 7.3 | 1.3 | 1.20 | 92.3 |
| Com. Ex. 5 | B-2 | water | 6.8 | 2.5 | 1.25 | 0.20 | 16 |
| Ex. 5 | B-2 | 1/15 M phosphoric acid buffer soln. | 7.4 | 6.9 | 1.25 | 1.10 | 88 |
| Com. Ex. 6 | B-3 | water | 7.0 | 3.1 | 0.7 | 0.05 | 7.14 |
| Ex. 6 | B-3 | 1/15 M phosphoric acid buffer soln. | 7.3 | 7.05 | 0.7 | 0.65 | 92.8 |
| Com. Ex. 7 | B-4 | water | 6.8 | 2.65 | 1.35 | 0.20 | 14.8 |
| Ex. 7 | B-4 | 1/15 M phosphoric acid buffer soln. | 7.4 | 7.1 | 1.35 | 1.15 | 85.1 |
| Com. Ex. 8 | C-1 | water | 7.6 | 3.05 | 2.3 | 0.45 | 19.5 |
| Ex. 8 | C-1 | 1/15 M phosphoric acid buffer soln. | 7.35 | 7.05 | 2.3 | 2.15 | 93.4 |
| Com. Ex. 9 | C-2 | water | 7.1 | 4.85 | 1.6 | 1.20 | 75 |
| Ex. 9 | C-2 | 1/15 M phosphoric acid buffer soln. | 7.45 | 7.40 | 1.6 | 1.50 | 93.7 |
| Com. Ex. 10 | C-3 | water | 7.25 | 3.30 | 1.7 | 0.25 | 14.7 |
| Ex. 10 | C-3 | 1/15 M phosphoric acid buffer soln. | 7.4 | 7.45 | 1.7 | 1.55 | 91.1 |
| Com. Ex. 11 | C-4 | water | 7.6 | 5.2 | 2.0 | 1.20 | 60 |
| Ex. 11 | C-4 | 1/15 M phosphoric acid buffer soln. | 7.35 | 7.50 | 2.0 | 1.90 | 95 |
| Ex. 12 | C-1 | 0.05% sodium citrate soln. | 7.65 | 7.20 | 2.3 | 2.10 | 91.3 |
| Ex. 13 | C-1 | 1/30 M phosphoric acid buffer soln. | 7.0 | 6.75 | 2.3 | 2.15 | 93.4 |
| Ex. 14 | C-1 | 1/30 M sodium acetate buffer soln. | 7.8 | 7.7 | 2.3 | 2.10 | 91.3 |
| Ex. 15 | C-1 | 0.02% NaHCO$_3$ solution | 8.1 | 7.9 | 2.3 | 2.0 | 86.9 |
| Ex. 16 | C-1 | 1/30 M phosphoric acid buffer soln. | 8.0 | 8.0 | 2.3 | 2.0 | 86.9 |
| Ex. 17 | C-1 | 1/30 M phosphoric acid buffer soln. | 6.0 | 5.85 | 2.3 | 2.25 | 97.8 |
| Ex. 18 | C-1 | 0.02% citric acid buffer soln. | 6.2 | 6.0 | 2.3 | 2.20 | 95.6 |

It is observed in Table 1 that according to the present invention, the amount of ligand released from the support is small and sterilized adsorbents of good quality for use in extracorporeal circulation treatment are obtained, even if the steam sterilization is conducted under severer conditions, namely at 121° C. for 40 minutes, than usual steam sterilization conducted at 121° C. for 20 minutes.

EXAMPLES 19 TO 32 AND COMPARATIVE EXAMPLES 12 TO 18

In a hard glass flask was placed 10 g (wet weight) of an adsorbent prepared in Reference Examples 1 to 11, and thereto was added 10 ml of a packing fluid shown in Table 2. The flask was sealed and allowed to stand in a thermostat maintained at 40° C. for 2 months.

The pH of the packing fluid and the amount of the ligand immobilized on the support were measured before and after allowing to stand. Also, the amount of substance eluted into the packing fluid (hereinafter referred to as "amount of solute" was measured after allowing to stand.

The results are shown in Table 2.

In addition to the ingredients used in the Examples, other ingredients can be used in the Examples as set forth in the specification to obtain substantially the same results.

What is claimed is:

1. A sterilized adsorption column for use in extracorporeal circulation treatment comprising a columnar container, an adsorbent comprising a water-insoluble support and a sulfated polysaccharide immobilized on said support through covalent coupling, and an aqueous solution of pH 5 to 9 containing 0.001 to 10% by weight of a buffer, said adsorption column being sterilized by packing said adsorbent and said aqueous solution in said container and heating the container with steam under a high pressure.

TABLE 2

|  | Adsorbent | Packing fluid | pH before | pH after | Amount of ligand (mg/ml) before | Amount of ligand (mg/ml) after | Amount of solute (p.p.m.) |
|---|---|---|---|---|---|---|---|
| Com. Ex. 12 | A-1 | water | 7.5 | 5.5 | 2.6 | 2.0 | 25 |
| Ex. 19 | A-1 | 1/30 M phosphoric acid buffer soln. | 7.4 | 7.4 | 2.6 | 2.5 | 15 |
| Com. Ex. 13 | A-2 | water | 7.2 | 2.8 | 1.2 | 0.20 | 30 |
| Ex. 20 | A-2 | 1/30 M phosphoric acid buffer soln. | 7.4 | 7.35 | 1.2 | 1.15 | 20 |
| Com. Ex. 14 | B-1 | water | 7.6 | 5.5 | 1.5 | 1.10 | 35 |
| Ex. 21 | B-1 | 1/30 M phosphoric acid buffer soln. | 7.35 | 7.4 | 1.5 | 1.45 | 25 |
| Com. Ex. 15 | B-4 | water | 7.0 | 3.5 | 1.55 | 0.20 | 65 |
| Ex. 22 | B-4 | 1/30 M phosphoric acid buffer soln. | 7.3 | 7.4 | 1.55 | 1.45 | 24 |
| Com. Ex. 16 | C-1 | water | 7.5 | 3.15 | 2.4 | 0.35 | 78 |
| Ex. 23 | C-1 | 1/30 M phosphoric acid buffer soln. | 7.4 | 7.45 | 2.4 | 2.25 | 33 |
| Com. Ex. 17 | C-3 | water | 7.2 | 3.5 | 2.35 | 0.40 | 72 |
| Ex. 24 | C-3 | 1/30 M phosphoric acid buffer soln. | 7.4 | 7.25 | 2.35 | 2.15 | 31 |
| Com. Ex. 18 | C-4 | water | 7.0 | 5.25 | 2.4 | 1.75 | 54 |
| Ex. 25 | C-4 | 1/30 M phosphoric acid buffer soln. | 7.4 | 7.45 | 2.4 | 2.3 | 23 |
| Ex. 26 | C-1 | 0.05% sodium citrate soln. | 7.65 | 7.4 | 2.4 | 2.25 | 28 |
| Ex. 27 | C-1 | 0.1% NaHCO$_3$ solution | 8.4 | 8.4 | 2.4 | 1.95 | 56 |
| Ex. 28 | C-1 | 1/30 M sodium acetate soln. | 7.8 | 7.8 | 2.4 | 2.05 | 46 |
| Ex. 29 | C-1 | 1/20 M H$_3$BO$_3$—Na$_2$CO$_3$ buffer soln. | 7.4 | 7.1 | 2.4 | 2.25 | 30 |
| Ex. 30 | C-1 | 0.05% sodium tartarate soln. | 7.8 | 7.6 | 2.4 | 2.10 | 32 |
| Ex. 31 | C-1 | 0.05% glycine soln. | 6.5 | 6.3 | 2.4 | 2.2 | 25 |
| Ex. 32 | C-1 | 0.05% sodium citrate-citric acid buffer soln. | 6.3 | 6.2 | 2.4 | 2.35 | 21 |

From the results shown in Table 2, it would be understood that even if adsorption columns for extracorporeal circulation treatment are stored for 2 months under a severer temperature condition as high as 40° C. than usual storage conditions, the amount of ligand released from the support and the amount of substances eluted into the packing fluid are small and the good quality of the column are maintained for a long term.

2. The adsorption column of claim 1, wherein the concentration of said buffer in said aqueous solution is from 0.01 to 2% by weight.

3. The adsorption column of claim 1, wherein said buffer is at least one member selected from the group consisting of citric acid, phosphoric acid, acetic acid, boric acid, tartaric acid, carbonic acid, maleic acid, glycine, and their salts.

* * * * *